(12) United States Patent
McGuire

(10) Patent No.: US 9,095,704 B2
(45) Date of Patent: Aug. 4, 2015

(54) ULTRAVIOLET LIGHT APPLICATOR SYSTEM AND METHOD

(75) Inventor: Kevin McGuire, Rochester, NY (US)

(73) Assignee: UV Technologies, LLC, Rochester, NY (US)

( * ) Notice: Subject to any disclaimer, the term of this patent is extended or adjusted under 35 U.S.C. 154(b) by 213 days.

(21) Appl. No.: 13/577,357

(22) PCT Filed: Nov. 19, 2010

(86) PCT No.: PCT/US2010/057460
§ 371 (c)(1),
(2), (4) Date: Aug. 6, 2012

(87) PCT Pub. No.: WO2011/063252
PCT Pub. Date: May 26, 2011

(65) Prior Publication Data
US 2012/0303102 A1    Nov. 29, 2012

Related U.S. Application Data

(60) Provisional application No. 61/262,570, filed on Nov. 19, 2009.

(51) Int. Cl.
*A61N 5/06* (2006.01)
*A61B 17/00* (2006.01)

(52) U.S. Cl.
CPC ............ *A61N 5/0603* (2013.01); *A61N 5/0624* (2013.01); *A61B 2017/00115* (2013.01); *A61N 2005/063* (2013.01); *A61N 2005/0606* (2013.01); *A61N 2005/0607* (2013.01); *A61N 2005/0661* (2013.01)

(58) Field of Classification Search
CPC ......... B01J 19/08; B01D 61/00; A61K 35/14; A61N 5/06; A61B 18/18; A61F 7/00
USPC .......... 422/186.3; 210/651; 424/532; 607/96, 607/88; 606/8; 128/898
See application file for complete search history.

(56) References Cited

U.S. PATENT DOCUMENTS

| | | | |
|---|---|---|---|
| 4,608,255 A * | 8/1986 | Kahn et al. | 424/532 |
| 6,277,337 B1 * | 8/2001 | Goodrich et al. | 422/186.3 |
| 6,991,644 B2 * | 1/2006 | Spooner et al. | 607/88 |
| 7,077,839 B2 * | 7/2006 | Hamblin et al. | 606/8 |
| 7,107,996 B2 * | 9/2006 | Ganz et al. | 128/898 |
| 7,217,366 B2 * | 5/2007 | Stoller et al. | 210/651 |
| 7,329,273 B2 * | 2/2008 | Altshuler et al. | 607/88 |

(Continued)

OTHER PUBLICATIONS

International Search Report from corresponding PCT Application No. PCT/US2010/057460.
Mitchell, et al., "Molecular response of nasal mucosa to therapeutic exposure to broad-band ultraviolet radiation," University of Texas MD Anderson Cancer Center, pp. 1-28.
Valam Corp. (Sponsor: New York Head & Neck Institute), "Laser Assisted Treatment of Chronic Sinusitis With and Without Light Activated Agents," pp. 1-4, ClinicalTrials.gov.

(Continued)

*Primary Examiner* — William Thomson
*Assistant Examiner* — Victor Shapiro
(74) *Attorney, Agent, or Firm* — Timothy W. Menasco, Esq.; Harter Secrest & Emery LLP

(57) ABSTRACT

A method of mitigating the effect of bodily pathogens including providing a light applicator including a housing, a power supply, and at least one light source wherein the light source is configured to emit light in the ultraviolet range when energized by the power supply, and directing the applicator toward a bodily orifice so as to directly irradiate the orifice for a period of time.

17 Claims, 7 Drawing Sheets

(56) References Cited

U.S. PATENT DOCUMENTS

| | | |
|---|---|---|
| 7,435,252 B2* | 10/2008 | Krespi et al. .............. 607/88 |
| 8,197,524 B2* | 6/2012 | Nakamoto et al. .............. 607/96 |
| 2002/0183729 A1 | 12/2002 | Farr et al. |
| 2006/0116669 A1* | 6/2006 | Dolleris .............. 606/17 |
| 2006/0153749 A1* | 7/2006 | Schroder .............. 422/186.3 |
| 2006/0167531 A1* | 7/2006 | Gertner et al. .............. 607/86 |
| 2008/0032252 A1 | 2/2008 | Hayman et al. |
| 2008/0058903 A1 | 3/2008 | Morgan |
| 2009/0018485 A1 | 1/2009 | Krespi et al. |
| 2009/0093865 A1 | 4/2009 | Krespi et al. |
| 2009/0118799 A1* | 5/2009 | Nanninga .............. 607/88 |

OTHER PUBLICATIONS

Wood, et al., "UV causation of melanoma in Xiphophorus is dominated by melanin photosensitized oxidant production," pp. 1-6, Porc Natl. Aca. Sci. U.S.A. Mar. 6, 2006.

Korytowski, et al., "Photoinduced Generation of Hydrogen Peroxide and Hydroxyl Radicals in Melanins," Photochemistry and Photobiology vol. 45, No. 2, pp. 185-190.

Mitchell, et al., "Ultraviolet A does not induce melanomas in a Xiphophorus hybrid fish model", Poc. Natl. Acad. Sci. U.S.A May 3, 2010, pp. 1-7.

* cited by examiner

ULTRAVIOLET LIGHT APPLICATOR SYSTEM AND METHOD

TECHNICAL FIELD

This present invention relates to the use of light as a treatment or supplement to destroy pathogens such as bacteria and viruses, for example, and, more particularly, to a system and method of treating and mitigating the effects of disease by applying ultraviolet light to bodily orifices such as the nasal passages, oral cavities, and ear canals. This patent application is a national stage application of PCT/US2010/057460 filed Nov. 19, 2010 and claims priority of U.S. Provisional Application Ser. No. 61/262,570 filed Nov. 19, 2009.

BACKGROUND INFORMATION

Light in the ultraviolet (UV) range (about 10 nanometers (nm) to about 400 nm) has been used to cure diseases since the 1870's. A Nobel Peace Prize was awarded to Niels Ryberg Finsen for his treatment of 300 people suffering from Lupus in Denmark. Kurt Naswitis irradiated blood with UV light through a shunt in 1922. In 1943, Emmett Knott, D. Sc was awarded U.S. Pat. No. 2,308,516, entitled "Method and Means for Irradiating Blood" which disclosed exposing blood particles to light in the ultraviolet range during transfusion therapy. These physicians, along with others over a 50 year span, performed over 300,000 clinical tests with no one dying from this treatment modality.

More recently, the University of Texas MD Anderson Cancer Center published a study entitled, "Molecular response of nasal mucosa to therapeutic exposure to broad-band ultraviolet radiation." In this study, human nasal mucosa and skin tissue samples were exposed to UVA (about 315 nm to about 400 nm) 23.8 mw, UVB (about 280 nm to about 315 nm) 8.2 mw, and UVC (about 100 nm to about 280 nm) 2.4 mw light at 100 and 1000 microjoules/mm^2, approximately 20 to 200 times the required dose needed to kill most viruses with 254 nm wavelength light. The study concluded, " . . . the UV induced DNA damage response of respiratory epithelia is very similar to that of the human epidermis and the nasal mucosa is able to efficiently repair UV induced DNA damage."

Another study relating to irradiation of the nasal passage, was sponsored by New York Head & Neck Institute and Valam Corporation, is entitled "Laser Assited Treatment of Chronic Sinusitis With and Without Light Activated Agents," and can be found at ClinicalTrials.gov, Identifier: NCT00948519. This study used NIR range laser light, to treat Rhinosinusitis, at levels 1000 to 10,000 times higher than is proposed by the present invention:

"Device: Laser+ICG

ICG arm—will be defined as local application on a pledget soaked with ICG with a concentration of 200 μg, upon removal of the pledget a NIR diode laser set at 6 W with light emittance introduced intranasally with a 30 mm diffuser fiber capable of radiating light circumferentially allowing the light energy to reach all treatable areas. Laser will be activated for 180 seconds. Assuming an approximate radius of the nasal cavity is 3 mm, energy density will be around 200 J/cm². Treatment will be repeated twice, 5-7 day apart. Cultures will be collected at the end of all treatments."

According to the U.S. Food and Drug Administration and the World Health Organization, brief exposure to UV radiation, about 5-15 minutes twice a week, is beneficial in helping the body produce vitamin D. However, the amount of exposure needed depends on several factors, including skin type, location, the time of day, and the time of year. FIG. 1 shows dark areas indicating high annual levels of UV exposure and relatively lighter areas indicating lower annual atmospheric levels of UV exposure. With large portions of the population spending increasing amount of time indoors, especially in the North and Northeast portions of the United States, and with increasing societal concerns about direct exposure to daylight, it is evident that a substantial number of Americans do not receive an equivalent amount of UV light as the rest of the world.

The amount of UV radiation emitted from the sun varies based on the time of year, time of day, location on earth, and weather conditions, among other factors. The U.S. Environmental Protection Agency publishes a UV index scale from 1-11 with one unit equivalent to 0.025 microwatts/mm^2. Considering the mean UV Index value is 5.5 or 0.1375 microwatts/mm^2, five minutes of exposure equates to 41.25 microjoules/mm^2 and fifteen minutes of exposure equates to 123.75 microjoules/mm^2.

In 2006, The World Health Organization published "Solar Ultraviolet Radiation," Environmental Burden of Disease Series, No. 13, Lucas, et al. which discloses that "Ultraviolet radiation is ubiquitous. Almost everyone has some exposure to ultraviolet radiation on a daily basis. It is an exposure we cannot entirely avoid and, anyway, to strive for zero exposure would create a huge burden of skeletal disease from vitamin D deficiency." Further, in "Sunlight 'D'ilemma: risk of skin cancer or bone disease and muscle weakness," Lancet, 2001; 357:4-6, Holick et al. estimate that exposure of the whole body in a bathing suit to one minimal erythemal dose ("MED") is equivalent to ingesting 10,000 IU of vitamin D wherein one MED is the dose of ultraviolet radiation ("UVR") required to produce a barely perceptible erythema in people with skin type 1, fair-skinned Caucasians who burn very easily and never tan (approximately 200 J/m^2 or 200 microjoules/mm^2 of biologically effective UVR). The MED for skin type V, Asian or Indian skin, is approximately 458 microjoules/mm^2.

In addition to known health benefits, in some instances, UV light may be able to kill and/or at least partially disable pathogens, germs, molds, bacteria, and/or viruses. The human immune system is well-suited to identify damaged, sterilized, and/or dead cells and remove them. However, certain viruses have the ability to cloak their presence making it difficult for the immune system to attack them. One such class of viruses may be those responsible for the common cold. Research has failed to conclusively demonstrate that products such as Airborne™ or high-dose zinc prevent or treat adult colds. Further, vaccines for the common cold are generally not practical because over 200 viruses cause the common cold and decongestants such as nasal or oral pseudoephedrine only treat symptoms, not the disease.

Accordingly, there is a need in the art for a safe system and method for treating various diseases and allergies that plague the human population, in particular diseases and allergies that enter through various bodily orifices such as the nasal, oral, and/or aural cavities.

BRIEF DESCRIPTION OF THE DRAWINGS

The present invention is disclosed with reference to the accompanying drawings, wherein.

Figure 1:
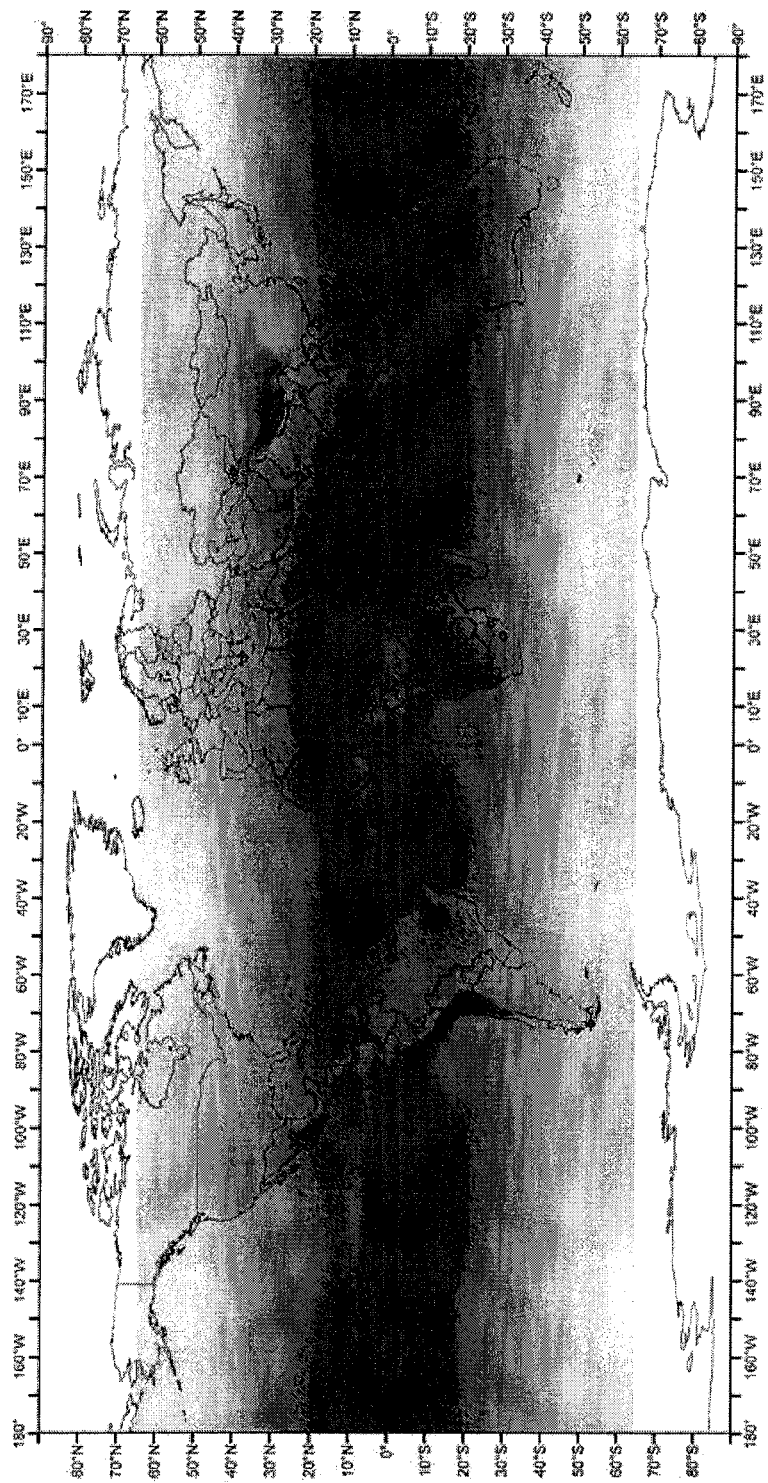
FIG. 1 is a plan view of the world showing ultraviolet light distribution based on location.

It will be appreciated that for purposes of clarity and where deemed appropriate, reference numerals have been repeated in the figures to indicate corresponding features.

DETAILED DESCRIPTION

The most likely area to contain the germs or viruses that cause the common cold are located on the nasal concha or turbinate. The turbinates compose most of the mucosal tissue of the nose and are required for functional respiration. The turbinates are enriched with airflow pressure and temperature sensing nerve receptors (linked to the "trigeminal" nerve route, the fifth cranial nerve), allowing for erectile capabilities of nasal congestion and decongestion, in response to climatic conditions and changing needs of the body, for example.

The turbinates are also responsible for filtration, heating, and humidification of air inhaled through the nose. Of these three, filtration is the most important reason to breathe through the nose. As air passes over the turbinate tissues, it is heated to body temperature, humidified (up to 98% water saturation), and filtered.

The respiratory epithelium which covers the erectile tissue (or lamina propria) of the turbinates plays a major role in the body's first line of immunological defense. The respiratory epithelium is partially composed of mucus-producing goblet cells. This secreted mucus covers the nasal cavities and serves as a filter by trapping air-borne particles larger than two to three micrometers. The respiratory epithelium also serves as a means of access for the lymphatic system which protects the body from infection by viruses or bacteria.

In addition, another area where diseases often forms is in the throat which manifests itself as a sore throat (pharyngitis). Common viruses, and even the viruses that cause mononucleosis (mono) and the flu, can cause a sore throat. Some viruses also produce blisters in the mouth and throat ("aphthous stomatitis"). A sore throat can also be caused by bacteria. The two most common bacteria to cause a sore throat are *Streptococcus* (which causes strep throat) and *Arcanobacterium haemolyticum*. *Arcanobacterium* causes sore throat symptoms mainly in young adults. Ear infections are also typically caused by bacteria.

Accordingly, the present invention effectively directs UV light to expose pathogens in the respiratory epithelium region, throat, and/or ear(s) and other locations where disease often forms, utilizing wavelengths and amounts preferably at or below amounts found to be safe and, preferably, commonly found in nature.

The safety and effectiveness of light in the ultraviolet range for treating infections, and mitigating the effects of pathogens, has been demonstrated previously but the present invention provides an unexpected advantage due to its emittance of wavelengths preferably at about 380 nm with a full width half maximum intensity of about 20 nanometers of light which stimulate the production of hydrogen peroxide through the process of photo-oxidation which, in turn, kills germs and other pathogens. The photo-oxidation process kills invading bacteria and viruses and generally does not effect surrounding cells. Researchers from Harvard University recently discovered the hydrogen peroxide also acts to signal white blood cells to the area to further fight pathogens and help prevent the onset of disease.

The production of Hydrogen Peroxide from the skin's exposure to UV light, Photo-Oxidation, has been studied for over 20 years. A landmark study was done by Setlow and Timmons et al UV Causation of melanoma in Xiphophororous is dominated by melanin synthesized oxidant production. demonstrates the rapid production of hydrogen peroxide of human skin cells when exposed to light and studies the wavelengths of UV light that cause photo-oxidation. Yet another study, is by W. Korytowski, B Pilas, et al. is entitled, "Photoinduced Generation of Hydrogen Peroxide and Hydroxyl Radicals in Melanins." In a healthy animal, the internal tissues, e.g. blood, brain, muscle, etc., are normally free of microorganisms. However, the surface tissues, i.e., skin and mucous membranes, are constantly in contact with environmental organisms and become readily colonized by various microbial species.

Some of the potentially harmful bacteria found in the nose and throat are: *Staphylococcus epidermidis*, *Staphylococcus aureus*, *Streptococcus mitis*, *Streptococcus salivarius*, *Streptococcus mutans*, *Enterococcus faecalis*, *Streptococcus pneumoniae*, *Streptococcus pyogenes*, *Neisseria* sp., *Neisseria meningitides*, *Enterobacteriaceae*, *Proteus* sp., *Pseudomonas aeruginosa*, *Haemophilus influenzae*, *Lactobacillus* sp., *Clostridium* sp., *Corynebacteria Mycobacteria*, *Actinomycetes*, *Spirochetes*, and *Mycoplasmas*. The challenge with using antibiotics to kill these germs is that along with the bad germs, the antibiotics also kill good germs. Also, each time a germ is exposed to an antibiotic the chance exists for a new strain of germ to grow that is resistant to the antibiotic. The number of documented viruses is about 5000. The estimated number of undocumented viruses is in the millions. Antibiotics do not work on viruses, vaccines are required, and a single vaccine works only on one virus. The common cold is caused by hundreds of different viruses. The costs associated with developing even a single vaccine are staggering and if the virus mutates the vaccine is ineffective. On the other hand, daylight is known to kill or disable most viruses.

It is no coincidence that studies have found hospital with an abundance of windows have a lower infection rate than darkened hospitals. Hospitals with windows let the sun shine in and it has been proven that even a small dose of sunlight kill germs. In fact, hospitals with an abundance of windows have been shown to have less bacteria than a darkened forest. Moreover, history points to outbreaks of deadly pandemics after volcanic eruptions and prolonged cold spells. It is also no coincidence that people are more healthy in the summer when they are more exposed to the sun.

According to the American Accreditation Health Care Commission, Adventist Health Care, Pro Health Care, Wake Forest University, Georgetown Department of Medicine: "We call it the common cold for good reason. There are over one billion colds in the United States each year. Colds can occur year-round, but they occur mostly in the winter, even in areas with mild winters. In areas where there is no winter, colds are most common during the rainy season. The relationship between sunlight and flu/colds and other airborne illnesses is clear; with less available sunshine, there is less of an opportunity for sunlight to kill the germs that cause sicknesses, and consequently more illness occurs.

Further, the University of Texas MD Anderson Cancer Center published a study entitled, "Molecular response of nasal mucosa to therapeutic exposure to broad-band ultraviolet radiation." In this study both human subjects and EpiAirway or nasal tissues were exposed to UV light. The study concluded, "Response of respiratory epithelia is very similar to that of the human epidermis." In other words, the skin in your nose is the same as the skin on your arms and has the same resistance and response to UV light.

With my invention the light is directed with precision to areas with high risk of infection. Exposures based on the quantity and delivery method of UV light can be recommended to maximize the amount of invading species that will be neutralized while minimizing the damage to the surrounding nasal cells. For example, studies have shown that as low as five microjoules or five microwatt*sec are required to destroy M13 bacteriophages and additionally only 6.6 microwatts*sec per mm^2 is required to kill 99% of the Influenza and Polio Virus at 254 nm wavelength light.

Figure 2:
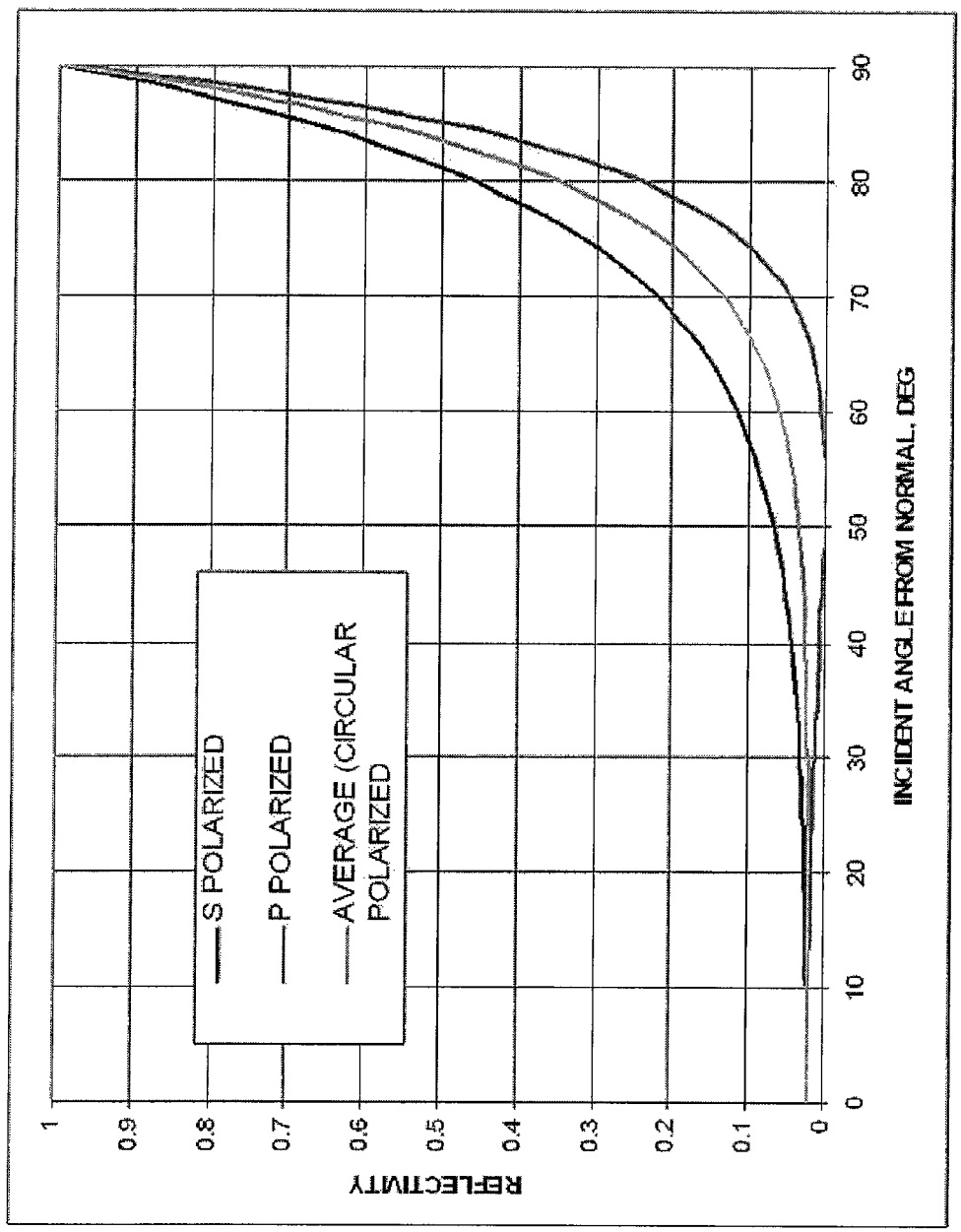
FIG. 2 is a graph showing resulting light based on incident angle and reflectivity.

Although 254 nm falls in the UVC range, there are no measurable amounts of UVC on the Earth's surface. In order for natural daylight and its UV component(s) to enter the nasal passages, some reflection needs to occur, the level of which is shown in FIG. 2. Typically, this reflection results from water, snow, and sand. For example, a person being outdoors for eight hours on the water, beach, or ski slopes, for example, on a day in which the UV index day is 5.5, experiences an average reflection of 10%, 15%, and 80% respectively, based on EPA estimates. Two percent of the reflected light from water, for example, entering the nasal passage, equates to a total of 57.6 microjoules/mm^2 of combined UVA and UVB light. This amount is less than one-third the level the World Health Organization states is necessary for the most fair-skinned person to show a change in skin color, less than $1/10^{th}$ the amount of UVC the MD Anderson study showed is safe, and on a lower level than the FDA considers beneficial, on average. Intuitively this result makes sense as even on the sunniest day, reports of sunburn in the nasal cavity are exceedingly rare.

Figure 3:
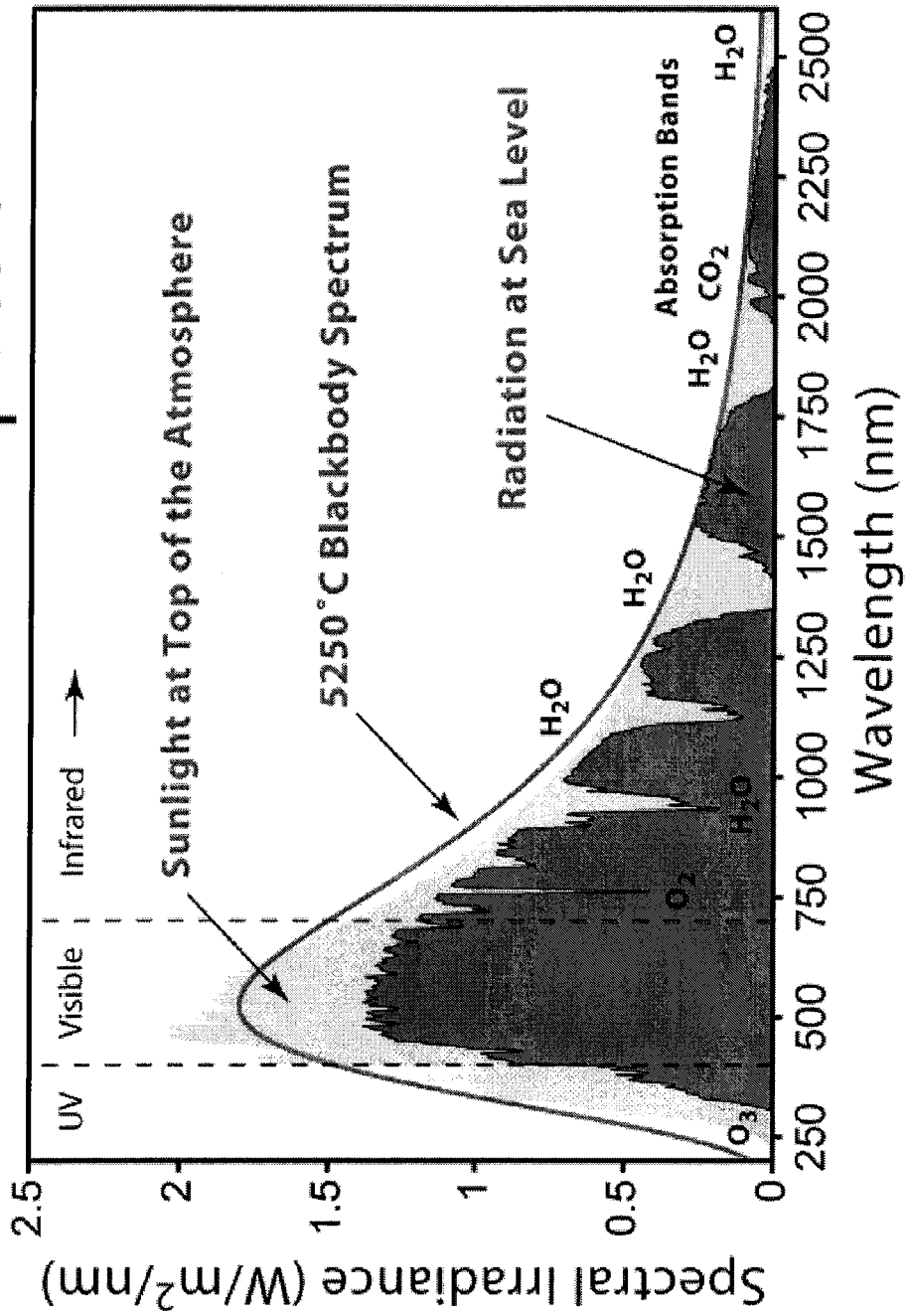
FIG. 3 is a graph showing an exemplary solar radiation spectrum.

Most published exposures of UV light on bacteria and viruses are at 254 nm wavelength, however, such a wavelength is shorter than what is typically found in nature. Wavelengths from about 280 to about 400 nm are typically found in nature and may be safer. FIG. 3 shows a solar radiation spectrum indicating an exemplary ultraviolet range.

Figure 4:
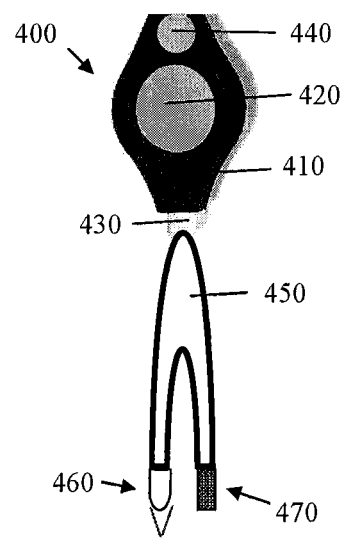
FIG. 4 is a plan view of a UV light applicator according to one exemplary embodiment of the present invention.
Figure 5:
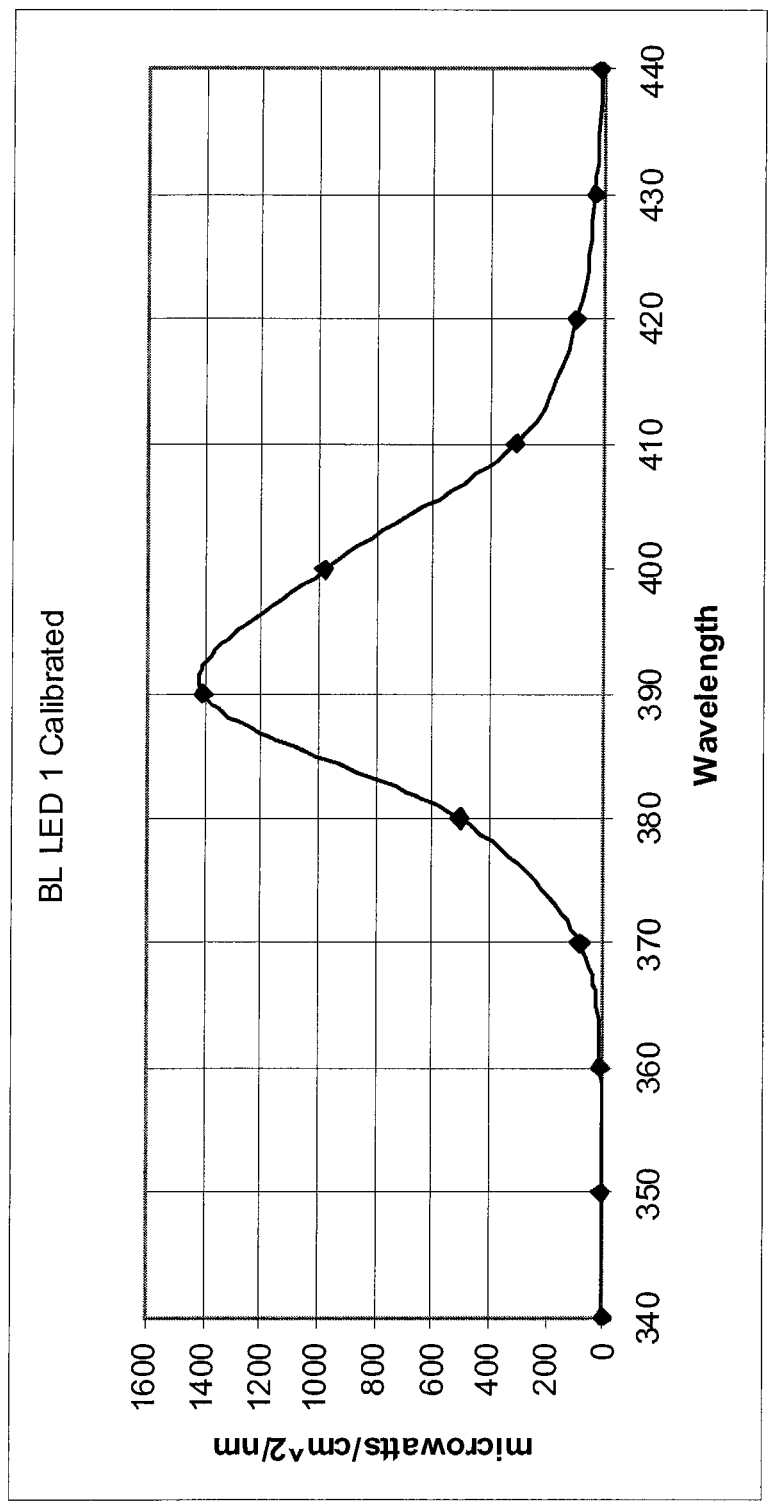
FIG. 5 is a calibration graph of a light source according to one embodiment of the present invention.

Referring to FIG. 4, a UV light applicator 400 according to one exemplary embodiment of the present invention is shown as including a housing 410, a power supply 420, such as a 3V lithium battery, at least one light source 430, such as a light emitting diode (LED), configured to emit light when energized, and a user interface 430, such as a button or finger pressure switch. Exemplary wavelengths of UV light emitted by the light applicator 400 range from about 250 nm to about 400 nm.

Still referring to FIG. 4, the UV light applicator 400 according to one exemplary embodiment of the present invention includes an optional light guide, such as a wishbone shaped light guide 450. The light guide 450 can be attached to the light applicator 400 proximate the light source 530, for example, or can be removably attached to the applicator 400 such as by snap, clip, press fit, or any other means of attachment. The light guide 450 can include reusable and/or disposable piping, lumen, and/or cannula and optionally includes one or more diffuse 460 or focusing 450 terminations to focus the light to a particular location and/or evenly distribute the light inside the bodily passage, respectively. In another embodiment, the applicator can include two or more light sources (not shown) separated such as by approximately one centimeter.

In yet another embodiment, the light applicator 400 can include circuitry for supplying power to the light source 430 for only a predetermined/prescribed amount of time. In another embodiment, the light applicator 400 can include a sound interface and device (not shown) for providing an audible sound indicating that the light source 430 has been energized for a predetermined amount of time. In yet another embodiment, a mirror (not shown) is disposed proximate, or attached to, the applicator 400 to allow the user to accurately direct the UV light.

In one exemplary embodiment, the UV light applicator 400 has a peak intensity of about 395 nanometers, a full-width half maximum of about 20 nanometers, and an output of 30 microwatts/mm^2. During a two second exposure, a bodily passage is exposed to about 60 microjoules/mm^2 which is on the order of a natural exposure and still less than $1/10^{th}$ the amount previously determined as safe.

In another exemplary embodiment, UV light is emitted by the applicator 400 so as to provide exposures of 10 to 100 microjoules/mm^2, which is less than $1/10^{th}$ the magnitude used in the University of Texas MD Anderson Cancer Center study, without the use of UVC light, laser(s), or a filtered light source. Other embodiments include exposures from 100 to 1000 microjoules/mm^2. Further embodiments include exposures of 1000 or more microjoules/mm^2. To ensure substantially equal exposure of UVA and UVB across devices, the spectrum of each device should be measured and the appropriate exposure time determined and indicated. For example, if one LED device had a peak spectrum shifted toward longer wavelengths, the required exposure time would be greater compared to another LED device centered on, for example, 380 nm with the same peak intensity. An exemplary calibration graph is shown in FIG. 6.

Figure 6:
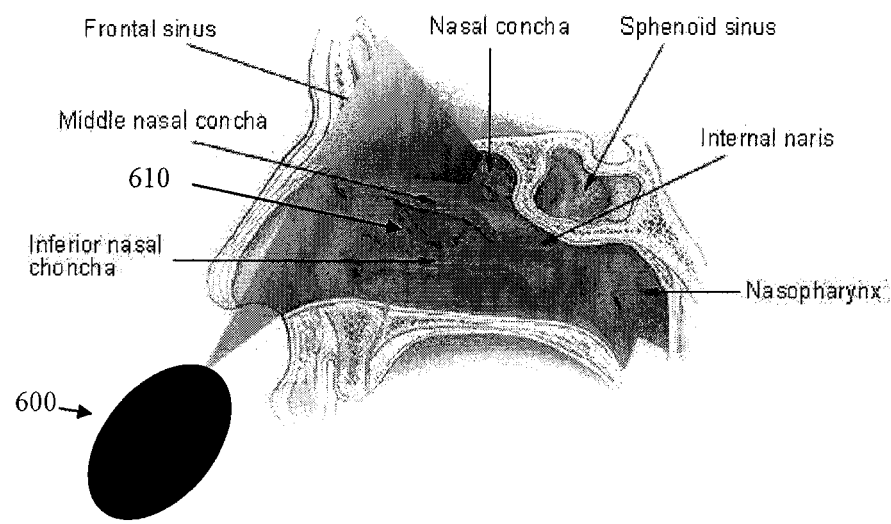
FIG. 6 is a plan view of a UV light applicator according to one exemplary embodiment of the present invention in use proximate the nasal cavity of a human body.

In one exemplary operation of the present invention, as shown in FIG. 6, UV light is emitted from a UV applicator 600 into one or more nasal passages 610 in order to mitigate the effects of the common cold and other air-born diseases and allergies. In this embodiment, the UV light applicator 600 is directed up each individual nostril for a prescribed exposure interval. Viruses and bacteria present on the respiratory epithelium will be exposed to the UV light and subsequently killed and/or disabled.

Figure 7:
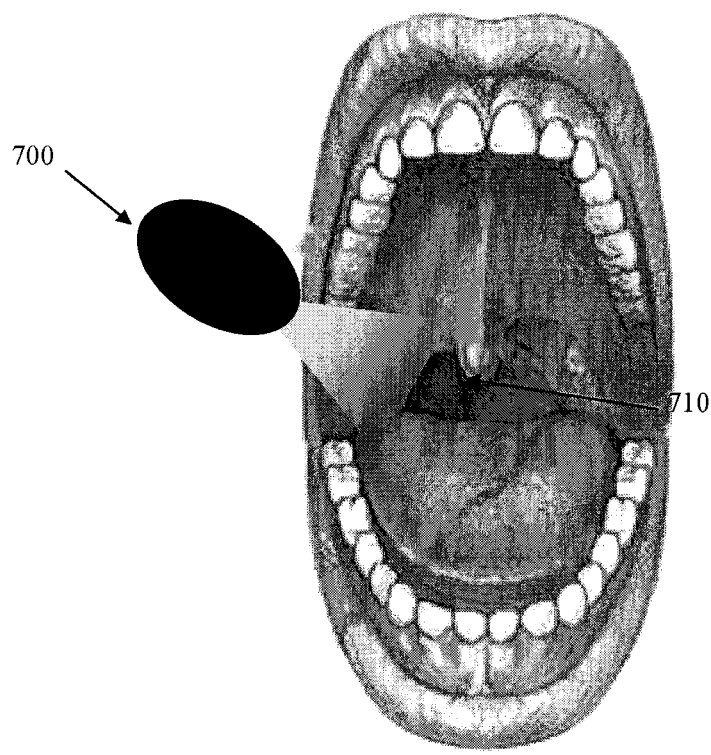
FIG. 7 is a plan view of a UV light applicator according to one exemplary embodiment of the present invention in use proximate the oral cavity of a human body.

In another exemplary operation, as shown in FIG. 7, a UV light applicator 700 can be directed into the throat area 710 for a prescribed exposure interval. In yet another exemplary operation, light emitted by a UV light applicator is directed into the ear (not shown) or any other bodily orifice and/or passage. The UV light, as described above, damages, sterilizes, and/or kills infecting cells directly or indirectly through photo-oxidation.

Figure 8:
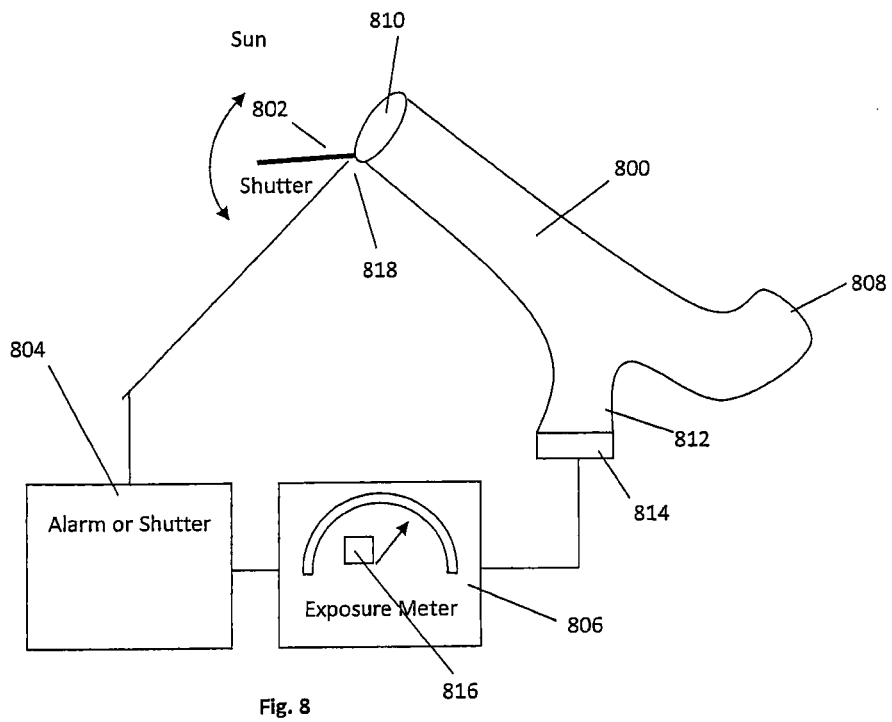
FIG. 8 is a plan view of a light guide according to one exemplary embodiment of the present invention.

In yet another exemplary embodiment as shown in FIG. 8, a light guide 800 is configured to be disposed proximate a bodily orifice at a first outlet end 808. Sunlight is received at an inlet end 810 and the light guide 800 redirects light toward bodily areas though the first outlet end 808. In the exemplary embodiment shown in FIG. 8, a photodetector 814 is disposed proximate a second outlet end 812 of the light guide 800. The photodetector 814 is configured so as to measure the amount of light directed toward the desired bodily area. The photodetector 814 is in electrical communication with at least one of an exposure meter 806 and/or an alarm 804 wherein the alarm 804 is in electrical communication with at least one of the photodetector 814 and/or the exposure meter 806 and can provide an audible visual, and/or tactile output, for example, based on the information electrically communicated by the photodetector 814 and/or exposure meter 806. Optionally, the alarm 804 can be configured to engage a shutter 802, such as by mechanical interaction, electrical communication with an actuator, or other means for converting an electrical signal into a mechanical force, for example, attached to the light guide 800 at a hinge 818 so as to substantially cover the inlet end 810 upon an alarm condition. The alarm condition can be communicated based on a predetermined level or, alternatively, based on user input. The predetermined level can be specified upon manufacture and stored in a data storage means or other electronic circuitry, or, alternatively, can be determined by the user through a user input device 816 disposed on one of the alarm 804 and/or the exposure meter 806. The exposure meter 806 can provide data representative of the amount of light indicated by the photodetector 814 such as by mechanical needle or other display. The alarm 804 and exposure meter 806 can be contained in the same or a separate housing.

Figure 9:
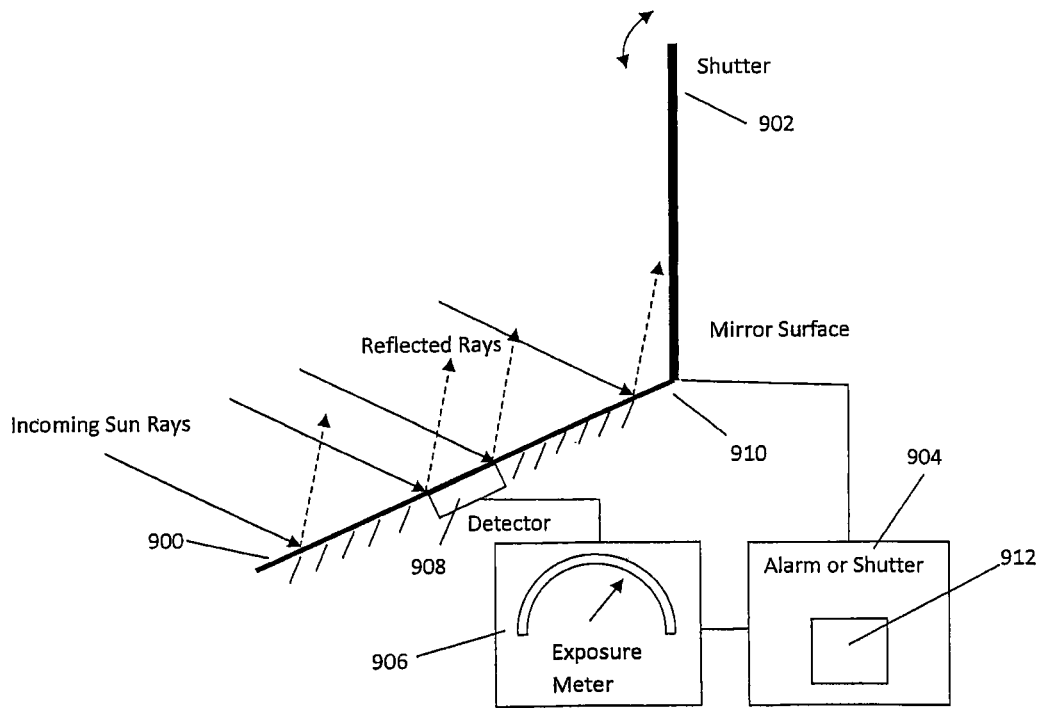
FIG. 9 is a plan view of a reflector according to one exemplary embodiment of the present invention.

Referring to FIG. 9, one exemplary embodiment of the present invention is shown as including a reflecting surface 900 configured to be disposed proximate a bodily orifice. Sunlight is received by the reflecting surface 900 and reflected toward the bodily orifice. A photodetector 908 is disposed proximate the reflecting surface and in electrical communication with at least one of an exposure meter 906 and/or an alarm 904 wherein the alarm 904 is in electrical communication with at least one of the photodetector 908 and/or the exposure meter 906 and can provide an audible visual, and/or tactile output, for example, based on the information electrically communicated by the photodetector 908 and/or exposure meter 906. Optionally, the alarm 904 can be configured to engage a shutter 902, such as by mechanical interaction, electrical communication with an actuator, or other means for converting an electrical signal into a mechanical force, for example, attached to the reflecting surface 900 at a hinge 910 so as to substantially cover the reflecting surface 900 upon an alarm condition. The alarm condition can be communicated based on a predetermined level or, alternatively, based on user input. The predetermined level can be specified upon manufacture and stored in a data storage means or other electronic circuitry, or, alternatively, can be determined by the user through a user input device 912 disposed on one of the alarm 904 and/or the exposure meter 906. The exposure meter 906 can provide data representative of the amount of light indicated by the photodetector 908 such as by mechanical needle or other display. The alarm 904 and exposure meter 906 can be contained in the same or a separate housing.

The embodiments described above can address allergic reactions, resulting from a suppression of T cell activity, for example, which I uniquely assert is due to the body's mobilization of pathogen-fighting agents, otherwise suppressed by the body, when an area has been irradiated by daylight. The mechanism by which the targeted bacteria, viruses, and other pathogens are mitigated can be by DNA destruction and photooxidation which produces pathogen-killing hydrogen peroxide.

The present invention has been tested as outlined below:
While suffering from a cold that had been going on for over three weeks, I decided to take a rest by lying down on a dock in the sun. Almost immediately after lying down, my nasal passages started to clear. I knew that something was different because I had been congested for several nights after lying in the same position. I was lying so that my feet were facing the sun which was low on the horizon. I positioned my head so that a maximum amount of sunlight could enter my nasal passage. I rested for about 15 minutes in this position. Afterwards, I still had nasal discharge for the rest of the day, but by two days later my cold was gone I was no longer experiencing the discharge. To rule out the possibility that this was just chance, and my cold was about to end regardless of irradiating my nasal passages, I tested my hypothesis by using UV LEDs with the wavelengths and power, as described above, to provide equivalent amounts of UV to the nasal passages in a reasonable and convenient amount of time.

Six days after the initial experience, I directed light emitted by a UV LED up both of my nasal passages for two seconds each. Prior to exposing my nose to the light, I had no discharge. After thirty seconds my nose started running. I blew my nose just once to clear the discharge (clear) and then about five minutes later felt a small amount of pressure in my sinus area that lasted for a minute. No other side effects were detected.

Seven days after the initial experience, I directed light emitted by a UV LED up both my nasal passages for two seconds each. Prior to exposing my nose to the light, I had no discharge. After twenty seconds my nose started running. I blew my nose only once to clear the discharge (clear) and then about 3 minutes later felt a small amount of pressure in my sinus area that lasted for about three minutes. No other side effects were detected.

Eight days after the initial experience I directed light emitted by a UV LED up both my nasal passages for two seconds each. Prior to exposing my nose to the light, I had no discharge. There was not enough discharge to require my clearing my nose, however, ten minutes later I felt a small amount of pressure in my sinus area that lasted for about five minutes. Fifteen minutes after treatment, I had enough discharge that required me to blow my nose. The discharge was clear. No other side effects were detected.

On all days, the only time I needed to blow my nose was after irradiating it with UV light. On all four occasions when light was directed up my nasal passages, I experienced a reaction. Further, three other subjects have exposed their nasal passages with UV light and all have reported a profound feeling in their nasal passages immediately after exposure with no other side effects.

Nearly a month after the first exposure to UV in my nasal passages, I exposed my throat to light emitted by a UV LED when I woke up with a sore throat. I exposed the throat for about four seconds waving the beam around in my throat. The relief to my throat was almost instantaneous with a faint aftertaste lasting for about ten minutes.

Accordingly, based on my observations and knowledge that UV light can be used kill bacteria and viruses, I have developed the light applicator system and methods of the present invention. In exemplary operations, the applicator system is used to direct light in the UV range up the nasal passage(s), oral cavities, and/or ear(s) in order to supplement naturally occurring light and cure, treat, curtail, and/or prevent the common cold and other air-born illnesses/diseases/pathogens that reside in the nose/throat/ear passage(s).

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A method of significantly mitigating the effects of common colds, influenza, sore throats, and ear infections primarily caused by airborne viruses and bacteria and comprising:

providing a light applicator including a housing, a power supply, and a light source when energized by the power supply emits light in the ultraviolet range consisting essentially only of UVA light and with a peak intensity of either about 380 nanometers or about 395 nanometers, each intensity with a full-width half maximum of about 20 nanometers, and an output of about 30 microwatts/mm2; and directing the applicator precisely to aim the light within bodily orifices selected from the nasal passages, the throat passage and the ear passages to directly irradiate the passages within the orifices for periodic times, the periodic time for each passage sufficient for the light to supply the passage at a power within a range from about 10 to about 1000 microjoules/mm2 of the UVA ultraviolet light and sufficient to stimulate the production of an effective amount of hydrogen peroxide by the passages through the process of photooxidation to kill pathogens but insufficient to adversely affect the passages.

2. The method of claim 1 wherein the periodic times consist of about two seconds for each nasal or ear passage and about four seconds for the throat passage.

3. The method of claim 1 wherein the light applicator further includes a user interface configured to communicate with the power supply and the light source so as to selectively energize the light source.

4. The method of claim 1 wherein the light applicator further includes an optical light guide removably attached to the applicator at the light source wherein the optical light guide includes at least one pipe, lumen or cannula for directing light emitted by the light source.

5. The method of claim 4 wherein the optical light guide is a wishbone shape having a first termination and a second termination wherein at least one of the terminations is selected from the group consisting of a focus termination configured to direct light to a particular location within the selected bodily orifice, and a diffuse termination configured to substantially evenly distribute light.

6. The method of claim 1 wherein the light applicator further includes a sound device and wherein the period of time is indicated by an audible sound emitted from the sound device.

7. The method of claim 1 wherein the emitted light supplies the selected bodily orifice within the range of 10 to 100 microjoules/mm2 of the ultraviolet light.

8. An ultraviolet light applicator for significantly mitigating the effects of common colds, influenza, sore throats, and ear infections primarily caused by airborne viruses and bacteria, by the applicator producing hydrogen peroxide through the process of photo-oxidation to kill pathogens but insufficient to adversely affect surrounding body cells, the applicator comprising:

a housing, a power supply, and a light source including a light emitting diode, the light source when energized by the power supply configured to emit light in the ultraviolet range consisting essentially only of UVA light and with a peak intensity of either about 380 nanometers or about 395 nanometers, each intensity with a full-width half maximum of about 20 nanometers, and an output of about 30 microwatts/mm2;

a user interface for selectively energizing the light source for periodic lengths of time to supply the UVA ultraviolet light to each nasal, ear and/or throat passage at a power within a range from about 10 to about 1000 microjoules/mm2 of the UVA ultraviolet light; and an optical light guide proximate the light source including at least one pipe, lumen or cannula to direct the emitted UVA ultraviolet light to the selected passages, each for the periodic times sufficient to stimulate the production of hydrogen peroxide by the body cells through the process of photo-oxidation to kill pathogens but insufficient to adversely affect the body cells.

9. The applicator of claim 8 wherein the optical light guide is a wishbone shape having a first termination and a second termination wherein at least one of the terminations is selected from the group consisting of a focus termination configured to direct light to a particular location within the selected bodily orifice, and a diffuse termination configured to substantially evenly distribute light.

10. The applicator of claim 8 further including a sound device configured to provide an audible sound upon the light source reaching the specified emittance.

11. The applicator of claim 8 and further comprising:
a light guide having an inlet end, a first outlet end and a second outlet end;
a photodetector disposed proximate the second outlet end;
an exposure meter in electrical communication with the photodetector; and
an alarm configured to receive an electrical communication from at least one of the photodetector and the exposure meter wherein the alarm is configured to emit a signal based on the electrical communication.

12. The applicator of claim 11 further including:
a shutter configured to communicate with the alarm, wherein the shutter is pivotably attached to the light guide; and
actuator means for rotating the shutter so as to substantially cover the inlet end of the light guide.

13. The applicator of claim 11 further including a user input device in communication with one of the exposure meter or alarm wherein the electrical communication is determined based on user interaction with the user input device.

14. The applicator of claim 8 and further comprising:
a light reflector having a reflecting surface;
a photodetector disposed proximate the reflecting surface;
an exposure meter in electrical communication with the photodetector; and
an alarm configured to receive an electrical communication from at least one of the photodetector and the exposure meter wherein the alarm is configured to emit a signal based on the electrical communication.

15. The applicator of claim 14 further including:
a shutter configured to communicate with the alarm, wherein the shutter is pivotably attached to the reflecting surface; and
means for rotating the shutter so as to substantially cover the reflecting surface.

16. The applicator of claim 14 further including a user input device in communication with one of the exposure meter or alarm wherein the electrical communication is determined based on user interaction with the user input device.

17. The applicator of claim 8, wherein the periodic times are from about two to about four seconds.

* * * * *